United States Patent [19]

Dodge et al.

[11] 4,036,231
[45] July 19, 1977

[54] THORACIC DRAINAGE UNIT WITH DEFOAMING MEANS

[75] Inventors: Larry H. Dodge, St. Charles; Byron G. Economidy, Manchester, both of Mo.

[73] Assignee: Sherwood Medical Industries Inc., St. Louis, Mo.

[21] Appl. No.: 633,873

[22] Filed: Nov. 20, 1975

[51] Int. Cl.² ............................................. A61M 1/00
[52] U.S. Cl. ............................. 128/276; 128/DIG. 5; 128/DIG. 24; 23/258.5 B
[58] Field of Search ................ 128/DIG. 5, DIG. 24, 128/275, 276

[56] References Cited

U.S. PATENT DOCUMENTS

| | | | |
|---|---|---|---|
| 3,520,300 | 7/1970 | Flower, Jr. | 128/276 |
| 3,545,440 | 10/1972 | Roslyn, Jr. | 128/276 |
| 3,699,815 | 10/1972 | Holbrook | 128/276 |
| 3,915,650 | 10/1975 | Talonn et al. | 23/258.5 |
| 3,918,912 | 11/1975 | Talonn | 23/258.5 |

*Primary Examiner*—John F. Pitrelli
*Assistant Examiner*—Robert F. Cutting
*Attorney, Agent, or Firm*—Stanley N. Garber; William R. O'Meara

[57] ABSTRACT

A thoracic drainage device including a container for receiving drainage fluid, and a drainage tube for connecting the pleural cavity of a patient to be drained to the container, the outlet end of the tube being disposed below the level of liquid in the container to provide a liquid seal. The container includes a gas outlet for connection with the atmosphere or to a source of vacuum, and an annular defoaming member in close surrounding relation with the drainage tube and in the flow path of gas flowing from the drainage tube to the gas outlet for minimizing foam.

16 Claims, 2 Drawing Figures

THORACIC DRAINAGE UNIT WITH DEFOAMING MEANS

BACKGROUND OF THE INVENTION

This invention relates to body fluid drainage devices and more particularly to thoracic drainage devices.

In thoractic drainage systems, a catheter is disposed within the pleural cavity of a patient and connected to a drainage collection container or bottle. In many cases, an initial amount of liquid is provided in the container and the catheter is connected to a drainage tube extending below the level of the liquid to provide a liquid seal. This liquid seal prevents the cavity from being in direct fluid communication with the atmosphere or a source of vacuum which may be used to assist in the draining of fluid from the cavity. One of the disadvantages of such an arrangement is that, should an air leak occur in either the cavity of the patient or in a tube connection between the cavity and the container, blood foam is generally produced that rises above the drainage liquid and tends to fill the interior of the container. Where a vacuum source is connected to the container for assisting the drainage fluid flow, the foam build-up is even more rapid. If allowed to fill the container, such foam may enter the vacuum source causing damage to it. Thus, a container filled with foam requires the connection of a new bottle even though the container could have held substantially more gas-free liquid. Because of the foam, such thoracic drainage devices require considerable monitoring to insure that foam does not accumulate such that it fills the container. Also, foam obscures the liquid level and it is more difficult to determine the actual amount of drainage liquid in the container when a significant amount of foam is present.

SUMMARY OF THE INVENTION

It is therefore an object of the present invention to provide a body fluid drainage device which substantially avoids the above-mentioned disadvantages.

A more specific object of the present invention is to provide a thoracic drainage device wherein foam in the container is reduced or minimized.

In accordance with the present invention, a body fluid drainage collection device is provided which includes a container having a gas outlet, passage means adapted for connection with a body cavity and extending into the container below a liquid level point therein, and defoaming means in the container in the flow path of fluid flowing from the passage means.

These and other objects and advantages of the present invention will become apparent from the following detailed description and drawing.

DESCRIPTION OF THE PREFERRED EMBODIMENT

Figure 1:
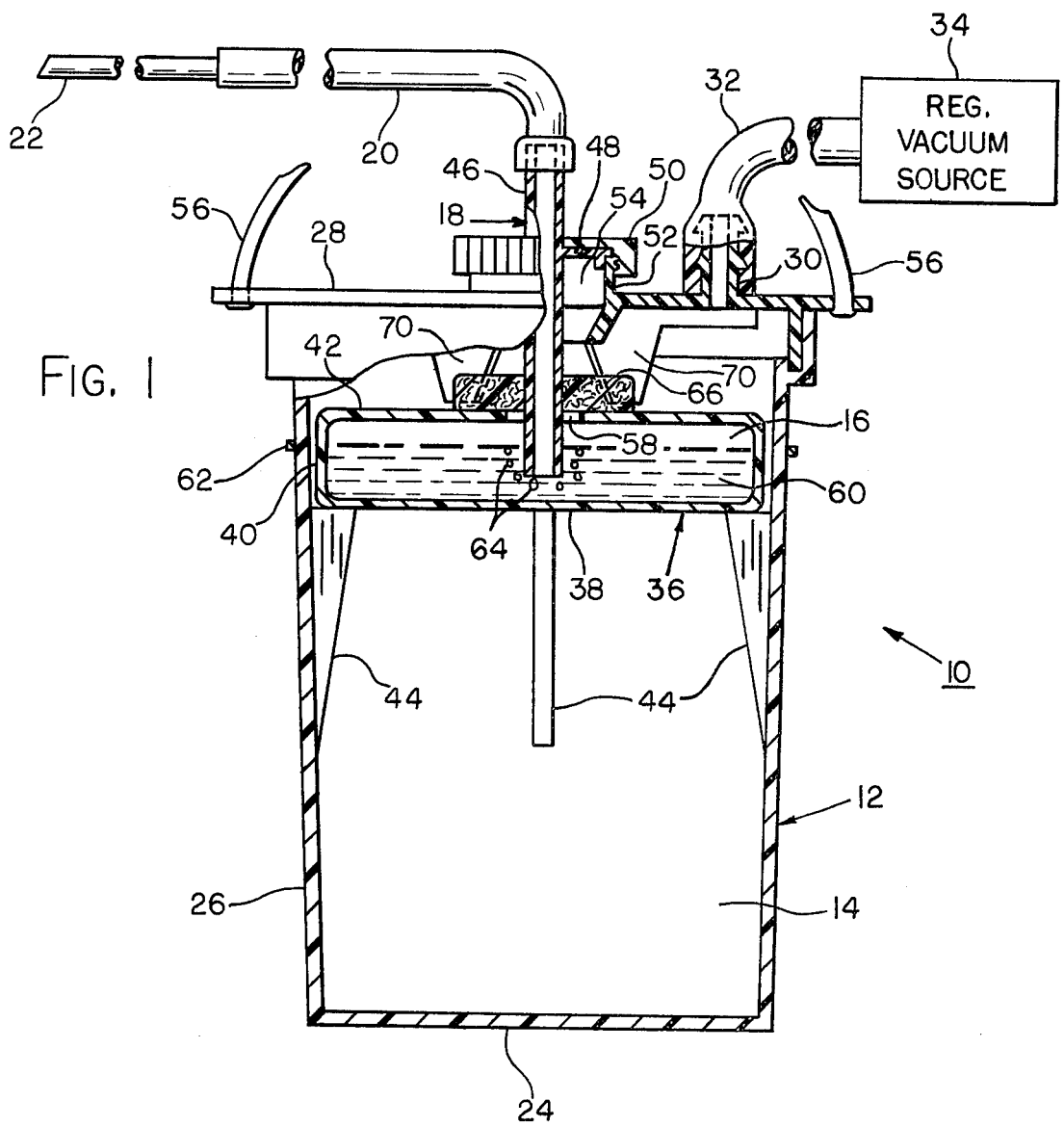
FIG. 1 is an elevational cross-sectional view of a thoracic drainage device in accordance with a preferred embodiment of the present invention.

Referring now to the drawing, and particularly to FIG. 1, there is illustrated a thoracic drainage device 10 which includes a container 12 having a collection chamber 14 and a liquid seal chamber 16 which is shown disposed in the upper portion of the container. A drainage fluid inlet member 18 communicating with the interior of container 12 is shown connected by a tube 20 to a catheter 22 that is adapted for insertion into the pleural or thoracic cavity of a patient to be drained. The container 12 has integral bottom and side walls 24 and 26 and an upper open end closed by a cover or lid 28 which may be spot-welded in sealed relation to the container. Lid 28 carries the fluid inlet member 18 and is provided with a gas outlet 30 shown including a tube connector or coupler connected to a tube or conduit 32 which is, in turn , connected to a regulated vacuum source 34. The gas outlet 30 may be connected directly to the atmosphere instead of to tube 32 and source 34 where the use of a negative pressure is not desired.

The liquid seal chamber 16 is shown in the form of a separate container 36 having a bottom wall 38, a side wall 40, and an upper wall or cover 42. The side walls 26 of the container 12 are each provided with an integral inwardly extending supporting rib 44, the ribs supporting the liquid seal container 36. The drainage inlet member 18 includes a fluid passage shown as drainage tube 46 having an integral sealing flange 48. A cap 50 sealingly engages the flange 48 and is threaded onto a neck 52 to attach the inlet member 18 and close a central opening 54 in the lid. A strap 56 is attached to the lid 28 for hanging the device from a support or from the patient.

The inlet or upper end of the drainage tube 46 is connected to the tube 20 so that tube 46 communicates with the catheter 22 and the body cavity to be drained. The drainage tube 46 extends downwardly through lid 28, into the container 12, through an opening 58 in the upper wall 42, and into the liquid seal chamber 16 with the outlet or lower end of the tube below the level of an initial quantity of a liquid 60, such as water or a saline solution. This initial quantity of liquid 60 may be poured through openings 54 and 58, which are in aligned relation, before the drainage member 18 is attached. Chamber 16 is initially filled to a level indicated by indicia mark 62 provided on the side wall 26 of container 12. The side wall of the container may also be provided with graduations (not shown) for visually determining the quantity of liquid drained. The tube 46 and the opening 58 are sized to provide a space between the walls of the opening and the tube for the flow of fluid out of the chamber 16 during operation of the device. Both containers 12 and 36, and lid 28 are preferably formed or molded of a relatively hard, transparent plastic, such as butadiene styrene or acetate butyrate styrene.

The thoracic drainage device thus for described is similar in construction and operation to that disclosed in U.S. Pat. application Ser. No. 619,109, filed Oct. 2, 1975, which is assigned to the assignee of this application. Briefly, in operation, when the catheter 22 has been placed in the pleural cavity of the patient, and the outlet 30 is connected to atmosphere or a vacuum is applied to the gas outlet 30 by source 34 as illustrated, drainage fluid, such as gas and/or liquid blood, flows from the body cavity through the catheter 22, tube 20, and tube 46. This drainage fluid flows from the outlet end of tube 46 into the liquid within the chamber 16. Liquid drainage will cause the chamber 16 to fill and overflow with the liquid flowing out of opening 58, over upper wall 42, and downwardly along the outer peripheral walls 40 toward the bottom of container 14. The side walls 40 of the liquid seal chamber are spaced from the container side walls 26 to permit the flow of liquid to the collection chamber 14. Any gas will flow from the outlet of tube 46, upwardly through the liquid adjacent the tube 46, as indicated at 64, through opening 58 to the upper portion of container 12 above chamber 16, and then through the gas outlet 30 to the vacuum source 34. The negative pressure of source 34 assists in drawing fluid from the patient's cavity and maintaining a negative pressure in the cavity for proper breathing.

Should the patient have a chest wound through which air flows to the pleural cavity or should air leak through a coupling or connection between the catheter 22 and tube 20 or between tube 20 and tube 46 which allows air to enter the tube 46, a considerable amount of air will bubble up through the liquid 60 along the tube 46. In order to prevent or minimize the production of foam caused by such flow of gas through the liquid 60, a defoaming member 66 is disposed in container 12 in the flow path of fluid from the outlet of tube 46 to the interior of container 12 above the upper wall 42. The defoaming member 66 is shown extending entirely around the tube 46 adjacent the top of wall 42 of the liquid seal chamber so that all fluid flowing from the outlet end of tube 46 must pass through the defoaming member after leaving chamber 16.

Drainage liquid, such as blood, flows in a relatively thin stream over the top of chamber 16 and into the collection chamber 14. The bottom portion of the defoaming member 66 engages wall 42 and is in the normal bloodstream or flow path of blood free of bubbles or air. The defoaming member extends above this liquid flow path and is in the flow path of gas to receive rising blood foam for separating the liquid or blood phase from the foam. Thus, the defoaming member is at and extends above the interface of the air or foam phase and the liquid phase so that all fluid including the foam must pass through it after leaving chamber 16.

Figure 2:
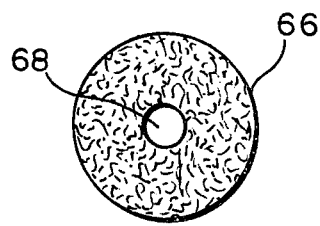
FIG. 2 is a top plan view of the defoaming member used in the drainage device of FIG. 1.

The defoaming member 66, as seen also in FIG. 2, is preferably an annular member of open-cell sponge material, such as an open-cell polyurethane foam. The defoaming member 66 is coated with a suitable defoaming agent such as a conventional anti-foam silicone grease. One such suitable defoaming agent is Anti-foam agent No. 20033 from the Dow Corning Corporation. The anti-foam agent may be applied by first mixing the silicone grease with freon, applying the mixture, and allowing the freon to evaporate.

Defoaming member 66 has a central opening 68, as seen in FIG. 2, which has a diameter slightly less than the outer diameter of tube 46 so that the defoaming member snugly contacts the tube 46 when installed in the drainage device of FIG. 1. In the illustrated embodiment, a plurality of circumferentially spaced, depending ribs 70, that are integral with the lid 28, engage the defoaming member 66 and urge the container 36 against the supporting ribs 44 to secure the container 36 in place. The ribs 70 are shown compressing small areas of the sponge-like defoaming member 66 against the wall 42 to secure it in place on top of the wall 42 and so that it extends over opening 58 of the liquid seal chamber 16, the member 66 completely closing the opening 58 around the tube.

As blood foam flows into the defoaming member 66, the bubbles break and the free gas passes upwardly through the defoaming member to the gas outlet 30 and then to the vacuum source 34 when used. In this way, foam is minimized and prevented from building up in the upper portion of the container 12 so that blood cannot enter gas outlet 30 and source 34. It is especially important to limit the amount of foam in a drainage device where the volume of the chamber above the liquid seal is relatively small, such as where the liquid seal chamber is above the collection chamber as in the construction of FIG. 1. However, even in drainage devices where the volume above the liquid seal is relatively large, foam can rapidly develop and fill the container, especially upon the occurrence of an air leak in the patient cavity or in the passageway from the cavity to the liquid seal.

As previously mentioned, where a substantial amount of foam is permitted to build up in a drainage device, not only is there danger of the foam and therefore liquid entering and causing damage to the vacuum source, but the foam makes it difficult or prevents an accurate visual determination of the amount of liquid drainage in the container. By preventing or limiting foam build-up, the amount of monitoring and change of drainage containers is also generally reduced.

While the radial space between the walls of opening 58 and tube 46 provides a simple and convenient passage arrangement for the flow of fluid from chamber 16, opening 58 and/or a different opening may be used if the defoaming member is arranged so that fluid from the chamber flows through it.

It will now be apparent that there has been provided an improved thoracic drainage device having a defoaming member which prevents or greatly reduces the production of blood foam. It should be understood that although the invention has been described with reference to the illustrated embodiment, modifications thereto may be made without departing from the true spirit and scope of the invention.

What is claimed is:

1. A thoracic drainage collection device comprising a container for collecting body fluid having a chamber adapted to receive an initial quantity of liquid therein, fluid passage means having an inlet for fluid communication with a body cavity to be drained, said fluid passage means extending into said chamber and having an outlet disposed below the level of the liquid in said chamber when said initial quantity of liquid is disposed therein so that all gas flowing from said fluid passage means flows into liquid in said chamber, gas outlet means on said container for passing gas out of said container, and defoaming means in said container in the flow path of substantially all gas flowing from said outlet to said gas outlet means.

2. The device of claim 1 wherein said passage means comprises a tubular member, and said defoaming means at least partially surrounds said tubular member.

3. The device of claim 2 wherein said defoaming means completely encircles said tubular member.

4. The device of claim 1 wherein said defoaming means comprises an open-cell sponge member of plastic material.

5. The device of claim 4 wherein said open-cell sponge member is coated with a defoaming agent.

6. The device of claim 1 wherein said chamber is in the upper portion of said container and is open at the top whereby drainage fluid can flow from the chamber and out the open top thereof and into a portion of the container below said chamber, and wherein said defoaming means extends above the open top of said chamber adjacent said passage means.

7. The device of claim 1 wherein said gas outlet means comprises tube coupling means for connecting the interior of said container with a source of negative pressure.

8. The device of claim 1 wherein said fluid passage means includes means for connecting said fluid passage means with the pleural cavity of a patient for draining blood and gas therefrom.

9. The device of claim 1 wherein said chamber has an upper wall within said container which has an opening for the flow of fluid out of said chamber and into a portion of the interior of said container, and said defoaming means completely covers said opening so that all fluid flowing therethrough flows into said defoaming means.

10. The device of claim 1 wherein said defoaming means is disposed in said container in a position such that all liquid and gas flowing from said chamber flows through said defoaming means.

11. The device of claim 1 wherein said defoaming means is disposed in said container such that substantially all gas flowing from said chamber to said gas outlet means must pass therethrough during operation of the device.

12. The device of claim 1 wherein said defoaming means is disposed in said container adjacent the exterior of said passage means and extends above the flow of gas-free blood and such that substantially all blood foam must pass therethrough during operation of the device.

13. A thoracic drainage collection device comprising a container for collecting body fluid having a chamber adapted to receive an initial quantity of liquid therein, fluid passage means having an inlet for fluid communication with a body cavity to be drained, said fluid passage means extending into said chamber and having an outlet disposed below the level of the liquid in said chamber when said initial quantity of liquid is disposed therein so that all gas flowing from said fluid passage means flows into liquid in said chamber, gas outlet means on said container for passing gas out of said container, and defoaming means in said container in the flow path of substantially all gas flowing from said outlet to said gas outlet means, said chamber having a top cover with an opening therein, said passage means comprising a tube extending through said opening and providing a radial space between the outer surface of said tube and the walls of said opening for the flow of fluid therethrough, and said defoaming means comprising a member of defoaming material surrounding said tube and in the contact with said tube and the upper surface of said top cover.

14. The device of claim 13 wherein said defoaming means is disposed at the interface between foam produced by air and drainage liquid, and drainage liquid free of air and flowing over said top cover.

15. The device of claim 13 wherein said defoaming material comprises open-cell plastic sponge coated with a defoaming agent.

16. The device of claim 13 wherein said defoaming means completely closes all portions of said opening between the outer surface of said tube and walls of said opening.

* * * * *